United States Patent [19]

Lang et al.

[11] 4,442,705

[45] Apr. 17, 1984

[54] CLAMPING NOSEPIECE FOR HARDNESS TESTER

[75] Inventors: Elliot R. Lang, Hamden; Edward L. Tobolski, Beacon Falls, both of Conn.

[73] Assignee: Page-Wilson Corporation, Bridgeport, Conn.

[21] Appl. No.: 388,213

[22] Filed: Jun. 14, 1982

[51] Int. Cl.³ ............................................. G01N 3/44
[52] U.S. Cl. ...................................................... 73/83
[58] Field of Search ................... 73/81, 82, 83, 84, 85

[56] References Cited

U.S. PATENT DOCUMENTS

| | | | |
|---|---|---|---|
| 1,806,767 | 5/1931 | Shore | 73/81 |
| 2,804,769 | 9/1957 | Clark, Sr. | 73/81 |
| 3,877,298 | 4/1975 | Narang | 73/81 |

*Primary Examiner*—S. Clement Swisher
*Attorney, Agent, or Firm*—Peter L. Berger

[57] ABSTRACT

A clamping nosepiece for a hardness tester is disclosed. The clamping nosepiece is removable from the tester and includes means to adjust the position of the penetrator with respect to the clamp. Additionally, the amount of clamping force with which the clamp holds the workpiece is also adjustable. Belleville washers having a stiff gradient are employed to exert the clamping force, and linear ball bearings are employed to minimize frictional hysteresis which can occur in prior clamping nosepieces.

10 Claims, 2 Drawing Figures

CLAMPING NOSEPIECE FOR HARDNESS TESTER

BACKGROUND OF THE INVENTION

This invention relates to a clamping nosepiece for machines which perform Rockwell hardness tests.

Rockwell hardness tests are performed on various workpieces to determine their hardness. Such machines generally comprise a C-shaped frame with a vertically adjustable anvil projecting upwardly from the bottom of the machine on which the workpiece sits.

A penetrator, often diamond, is attached to the head or top of the machine and after suitable preparation, the penetrator penetrates into the workpiece held on the anvil under application of the "major load". The depth of penetration is related to the hardness of the material being tested.

In order to ensure accuracy in the testing procedure, it is necessary to hold the workpiece steady while the major load is applied. In some cases, this is done by an operator manually holding the workpiece and using the diamond penetrator to bear on the top of the workpiece sufficiently to hold it in place. The approach is not satisfactory because the operator can not ensure against movement during the test, the workpiece may not be rigidly held in place and using the penetrator to hold the workpiece down introduces its own error into the process. Although the holding force required for certain operations can be accommodated manually, in other cases it cannot.

One approach to providing a clamping nosepiece is identified in U.S. Pat. No. 2,804,769 issued to C. W. Clark, Sr. entitled "Hardness Tester Work Piece Clamping Means". That patent describes a clamp which includes a collar 41 to bear against the workpiece 25 supported on an anvil 11. The collar 41 is part of a nose piece assembly comprising a tube 43 and flange member 46 which are fixedly connected to the head of the machine as shown at 47. A compression spring 42 has one end bearing against the top of collar 41 and the other end bearing against the bottom of the housing. The tension in the spring is controlled at the top by rotating tube 43 in flange 46 to adjust the pressure bearing against the top of the spring. One disadvantage of the Clark system is that the nosepiece is fixedly connected to the head of the tester.

Since there are many cases when a clamp is not required, such a fixed connection limits the versatility of the machine. Another problem is that the manner in which the compression spring bears against the collar 41 leads to inaccuracies in conducting measurements. This is due to the limited force which can be brought to bear on the small bearing surface of the collar on which the spring rests. Therefore, a slight tilting in the workpiece may not be properly compensated since the pressure may not be enough to force the surface of the workpiece to be so-oriented so as to be exactly perpendicular to the movement of the penetrator. Another problem of the Clark device is that the positional relationship between the tip of the penetrator and that of the collar is not adjustable. This can present problems since all diamond needles are not exactly the same size. Still further, it is preferable to be able to vary the force of the clamp on the workpiece prior to applying the minor load. This will allow for varying the clamping force by using the clamp rather than using the penetrator movement to vary the force. Another problem associated with the Clark device is that movement of the clamp with respect to the penetrator is through relative frictional movement between collar 41 and tube 43. Repeated up-down movement of these members results in a frictional hysteresis which can affect the actual hardness test measurements.

U.S. Pat. No. 3,877,298 was issued on Apr. 15, 1975 to Rajendra K. Narang and is entitled "Workpiece Clamp and Tool Shielding Device and Combination Thereof With a Tool Applying Apparatus". That clamp represented an improvement over the Clark system in that the clamp nose was removable from the head by using a pair of manually operating clamping screws which connect the clamping nose assembly to the head of the machine. Additionally, the Narang system provides a wide compression spring 27 bearing against a wide flange 21, the wide flange being formed as part of sleeve 20. Narang posits that the wide flange eliminates rocking or cocking of the sleeve on the workpiece, which it stated to be an advantage over the prior art. The other problems associated with the prior art are not recognized or addressed by the Narang system. Additionally, use of the widened flange 21, while allegedly providing benefits also causes the Narang system to be unwieldly.

An object of the present invention is to provide a clamping nosepiece which is compact in design.

Another object of the present invention is to provide such a nosepiece which is removable from the head of the tester.

Still another object of the present invention is to provide such a nosepiece in which the amount of holding force on the workpiece can be adjusted.

Another object of the present invention is to provide such a nosepiece in which the position of the penetrator with respect to the clamp is adjustable.

Yet another object of the present invention is to provide such a clamping nosepiece in which the deleterious affects of frictional hysteresis are substantially eliminated.

Another object of the present invention is to provide such a nosepiece which securely clamps the workpiece so that rocking or cocking of the workpiece is prevented.

Still another object of the present invention is to provide such a nosepiece in which adjustments can be made for different sized penetrators to eliminate their breaking.

Other objects, advantages and features of the invention will become more apparent thereinafter.

SUMMARY OF THE INVENTION

In accordance with the principles of this invention, the above objects are accomplished by providing a clamping nosepiece which is attachable to the plunger sleeve of the hardness tester with a manual operated screw. The clamping nosepiece assembly includes a body secured to the sleeve and a housing rotatably coupled to the body. When the housing is rotated with respect to the body, the position of the clamping nosepiece is vertically adjusted to adjust the positional relationship of the penetrator with respect to the clamp. Additionally, the housing and clamp which move together with respect to the guide for the penetrator do so through a linear ball bearing which materially reduces the frictional hysteresis. A Belleville washer assembly (a high gradient spring) provides the clamping force and its arrangement in the nosepiece assembly and enables a compact and efficient clamping means to be provided. When the positional relationship of the nosepiece is adjusted with respect to the clamp, the amount of force exerted by the Belleville washer is also adjusted so that the clamping force on the workpiece can easily be adjusted.

DETAILED DESCRIPTION

Figure 1:
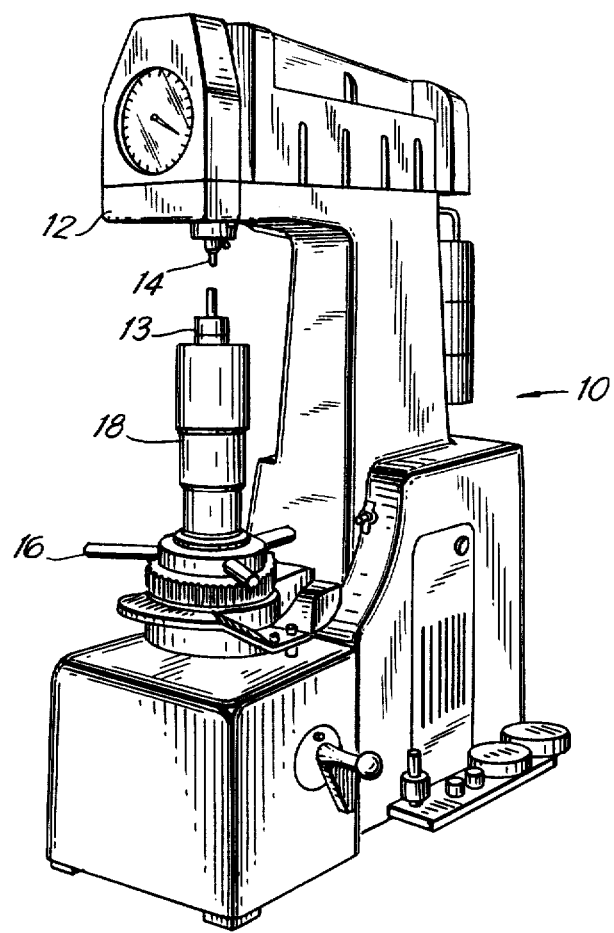
FIG. 1 is a side view of a hardness tester including the attachable clamping nosepiece.

FIG. 1 illustrates a conventional hardness testing machine 10 having a C-shaped frame which may be formed of cast iron, cast parts or the like. The machine 10 is merely illustrative of similar machines and is used with the present invention. Generally, all such machines include a head 12 and a workpiece supporting anvil 13 rising up from the bottom of the frame. A penetrator 14, preferably diamond, extends downwardly from the head. The anvil is vertically moved by an operator turning elevating screw 16 which vertically moves telescoped assembly 18 on which the supporting anvil is carried.

In general, these machines are operated by placing the workpiece to be tested on the anvil and raising the anvil until it contacts the penetrator. The depth of the initial penetration is slight, and this is the minor load applied to the workpiece. A corresponding guage or dial is then set, and the major load is then applied to the penetrator. The reading on the guage related to the depth of penetration is a measure of the hardness of the material.

Figure 2:
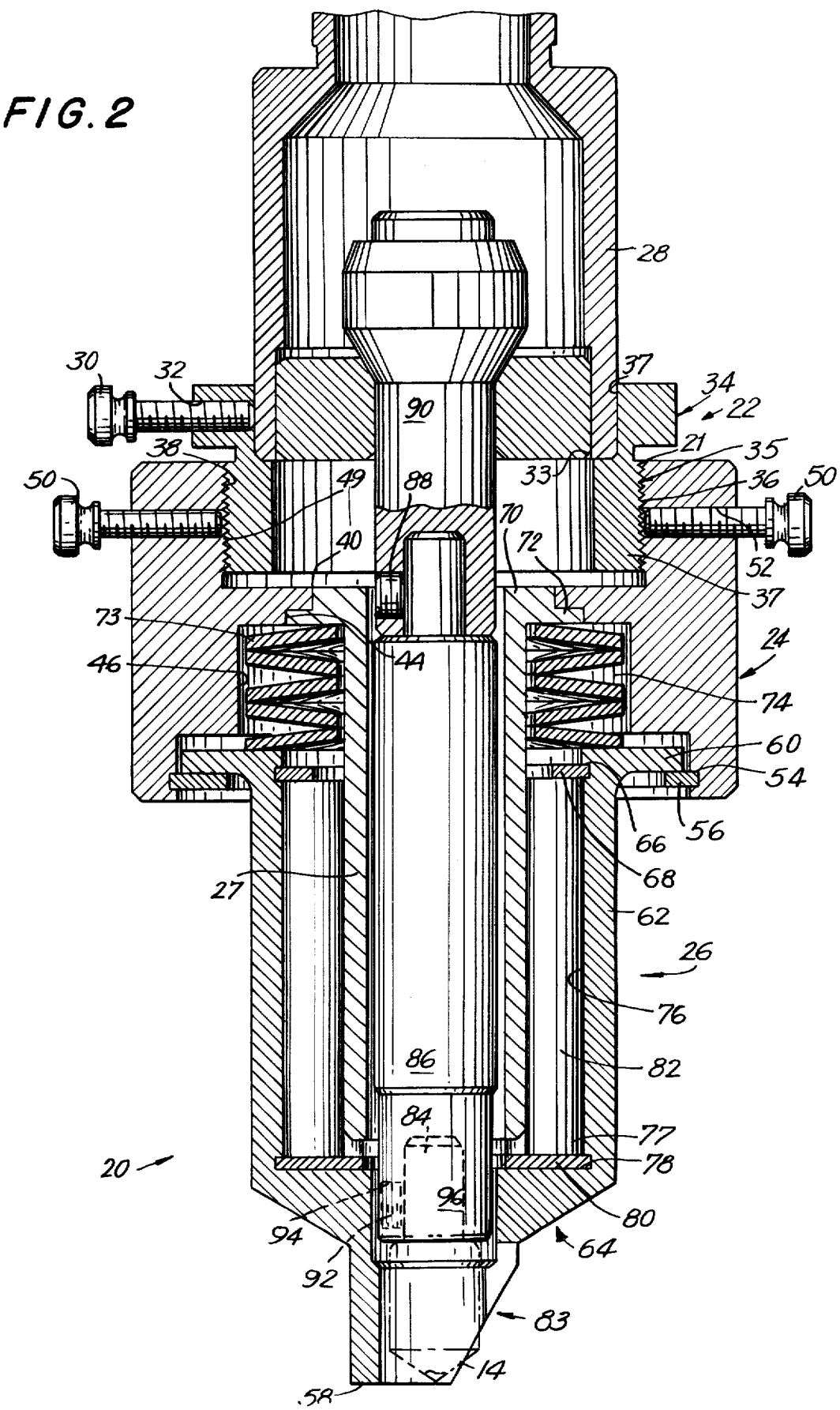
FIG. 2 is a sectional view along lines 2—2 of FIG. 1 showing the details of the clamping nosepiece assembly of this invention.

FIG. 2 is a sectional view of the clamping nosepiece assembly 20 of this invention. One of the important aspects for an accurate reading is the stability of the workpiece during the test. Frequently, movement of the workpiece can occur, and this leads to inaccuracies in the measurements.

Still further, if the surface of the workpiece being tested is other than perpendicular to the penetrator other inaccuracies develop. Consequently, a rigid clamping mechanism is desirable.

The clamping nosepiece 20 comprises three main elements which are a body 22 attachable to the frame of the machine, a housing 24 connected below the body and including the clamping nosepiece 26 and a nose clamp guide 27 coaxial with the body 22 and housing 24. The guide surrounds the penetrator 14.

The clamping nosepiece 20 is attached to the plunger sleeve 28 which partially extends out of the head 12 of the machine. A knurled screw 30 passes through a threaded passage 32 formed in the upper portion of the body 22, and this enables the entire clamping nosepiece assembly to be readily removed from the testing machine.

The body comprises an annulus having an upper shoulder 34 and lower neck portion 35. A seat 33 is formed in the inner wall 37 to receive the plunger sleeve 28. The body further comprises a threaded section 36 on the peripheral surface 37 of the neck portion 35 which engages a corresponding threaded section 38 formed in the housing 24.

The housing 24 also comprises an annulus which has a bore 40. The interior wall of the housing 24 below the bore 40 comprises a series of outward steps 44, 46 and 48, which will be described later.

Threaded section 38 formed on the interior wall 49 of a bore formed in the upper portion of housing 24 engages threaded section 36 to permit the housing to move vertically with respect to the body as the housing is rotated. A pair of knurled screws 50 pass through threaded passages 52 formed in the upper portion of the housing. The passages 52 terminate at the interior wall 49. In order to set the positional relationship between the body and housing, knurled screws 50 are tightened against threaded section 36 of the periphery 37 of the neck portion of the body.

An annular notch 54 is formed in the step portion 48 of the interior wall of the housing. A retaining ring 56 is inserted in the notch to carry the clamp 26. The clamp is a generally annular member having a flange 60 formed at its head, a cylindrical center neck portion 62 terminating in an inwardly tapered sleeve 64. Flange 60 abuts retaining ring 56. Additionally, a notch 66 is formed in interior wall of clamp 26 approximately level with the flange 60. Another retaining ring 68 is inserted in notch 66, the function of which will become more apparent hereinafter.

The outer wall of noseguide 27 includes a small outward step 72 forming the shoulder 70 which mates with the inner wall step 44 of the housing. An annular cavity 74 is formed between the periphery of noseguide 27 and second step 46 of the housing.

A very stiff spring 73 having a high gradient is inserted in this annular cavity 74, and one preferred spring is formed by using a set of stacked Belleville washers. The force exerted by this spring for its displacement is great, and the compact nature of the formed annular cavity 74 and spring 73 allows a significant clamping force to be provided in a compact fashion. The top of the spring 73 bears on shoulder 70 of noseguide 27 while the bottom of the spring bears on flange 60 of the clamp 26.

The inner wall 76 of clamp 26 is cylindrical and a cavity 77 is formed between the periphery of the noseguide 27 and the inner wall 76 of the clamp. The inner wall 76 terminates downwardly at a base 78 on which a support ring 80 is located.

A linear ball bearing 82 is held in the cavity 77, with the top of the ball bearing bearing against retainer ring 68 while the bottom of the ball bearing rests on support ring 80.

The lower tip 58 of the clamp 26 is partially cut out as at 83 to permit easy viewing of the top of the diamond penetrator 14.

The penetrator is mounted in a bore 84 formed in the bottom of an extension plunger 86, the extension plunger being secured to the nosepiece clamp by means of a set screw 88 threaded through a portion of the seating column 90 which is part of the head of the tester and does form a part of this invention. Similarly, a set screw 92 carried in a hollow 94 at the lower end of the extension plunger bears against the head 96 of the diamond penetrator to fix it in place with respect to the plunger.

The operation of this clamping nosepiece invention will now be described. The nosepiece clamp is fastened to the head of the machine by tightening knurled screw 30 to bear against plunger sleeve 28. It is assumed that the diamond penetrator is already loaded into the extension plunger and the workpiece has been raised on the anvil. In order to adjust the tip of the penetrator with respect to the clamp 26 housing 24 is rotated with respect to body 22. As the housing 24 moves vertically, it carries the entire nosepiece assembly. The nosepiece assembly 26 moves including noseguide 27.

Thus, the position of the tip of the penetrator can be easily adjusted, and it can be recessed any reasonable amount. This same mechanism can also be used to adjust the clamping force exerted on the workpiece by the nosepiece 26 prior to setting the minor load. Since the penetrator 14 is always at the same point with respect to the workpiece when the minor load is applied, the clamping force can be adjusted by adjusting the amount of recess of the penetrator. When the anvil 13 is raised, it first contacts tip 58. The downward force on the tip 58 is controlled by the spring 73 and the amount that the penetrator is displaced relative to tip 58 can be adjusted. Therefore, when the workpiece bears against tip 58, it will move more or less upwardly according to the amount that penetrator 14 is recessed, and therefore, the clamping force will be adjusted.

Use of the linear ball bearing 82 materially reduces the friction between the moving nosepiece clamp 26 and the guide 27 which significantly minimizes the frictional hysteresis developed in the prior art apparatus. As the workpiece bears on tip 58, the tip begins to rise with respect to penetrator 14. Guide 27 remains in place during this movement, and linear ball bearings 82 are located between the moving nosepiece 26 and noseguide 27. Additionally, use of the friction-free linear bearings allows for better accommodation to unevenness in the surface of the workpiece when the additional clamping of the spring is employed. Center-line application of the clamping force in conjunction with the stiffer gradient spring also enhances the clamping capability.

Although this invention has been described with certain illustrative elements, such elements are not limiting the actual invention. Substitution of equivalent elements and components may be made by those of skill in the art without departing from the scope and spirit of this invention.

What is claimed is:

1. A clamping nosepiece for a hardness tester, said hardness tester being conventional and having a head and an anvil connected to its base, a workpiece supported on said anvil and being raised thereon to contact the tip of said clamping nosepiece and be clamped thereby with a clamping force, said tester further comprising a penetrator recessed in said clamping nosepiece, said clamping nosepiece comprising:
   attachment means to attach said clamping nosepiece to the head of the hardness tester, and
   adjustment means coupled to said clamping nosepiece to adjust the position of the penetrator with respect to the tip of said clamping nosepiece to adjust the amount said penetrator is recessed in said clamping nosepiece,
   wherein said adjustment means comprises a body attached to said head of the tester, said penetrator being fixedly attached to said body, a housing vertically adjustably coupled to said body, said nosepiece being coupled to said housing so that as said housing is vertically adjusted with respect to said body said nosepiece is adjusted with respect to penetrator, the position of the penetrator being adjusted independent of the clamping force.

2. A clamping nosepiece as set forth in claim 1, wherein said attachment means comprises means to remove said clamping nosepiece from said head of the tester.

3. A clamping nosepiece as set forth in claim 1, wherein said body comprises an annulus having a threaded section on a peripheral surface thereof, said housing also comprising an annulus with a threaded section on an interior wall thereof to engage the threaded section of said body.

4. A clamping nosepiece as set forth in claim 3, further comprising passages in said housing and manually operated screws passing through passages to said body to fix said body with respect to said housing.

5. A clamping nosepiece as set forth in claim 2, further comprising clamping adjustment means to adjust the clamping force exerted by said nosepiece on said workpiece.

6. A clamping nosepiece as set forth in claim 5, wherein said clamping adjustment means comprises a spring having a stiff gradient.

7. A clamping nosepiece as set forth in claim 6, wherein said spring comprises a Belleville washer type spring.

8. A clamping nosepiece for a hardness tester, said hardness tester being conventional and having a head and an anvil connected to its base, a workpiece supported on said anvil and being raised thereon to contact the tip of said clamping nosepiece and be clamped thereby with a clamping force, said tester further comprising a penetrator recessed in said clamping nosepiece, said clamping nosepiece comprising:
   attachment means to attach said clamping nosepiece to the head of the hardness tester, and
   adjustment means coupled to said clamping nosepiece to adjust the clamping force that said clamping nosepiece exerts on said workpiece independent of the position of the penetrator.

9. A clamping nosepiece as set forth in claims 1, 2, 5 or 8 further comprising linear ball bearing means mounted between said clamping nosepiece and said penetrator to minimize frictional hysteresis as said clamping nosepiece moves relative to said penetrator.

10. A clamping nosepiece as set forth in claims 1 or 8 wherein the tip of said clamping nosepiece is partially cut out to permit viewing of said penetrator.

* * * * *